US012586681B2

(12) United States Patent
Masoud et al.

(10) Patent No.: US 12,586,681 B2
(45) Date of Patent: Mar. 24, 2026

(54) CLINICAL PERSONAL PROTECTIVE EQUIPMENT WITH INTEGRATED DISPLAY AND MEDICAL DEVICE CONTROL SYSTEM

(71) Applicant: The Research Foundation for the State University of New York, Albany, NY (US)

(72) Inventors: Hesham Masoud, Syracuse, NY (US); Andrew Decker, Cambridge, MA (US)

(73) Assignee: The Research Foundation for the State University of New York, Albany, NY (US)

( * ) Notice: Subject to any disclaimer, the term of this patent is extended or adjusted under 35 U.S.C. 154(b) by 207 days.

(21) Appl. No.: 18/590,166

(22) Filed: Feb. 28, 2024

(65) Prior Publication Data

US 2024/0290484 A1 Aug. 29, 2024

Related U.S. Application Data

(60) Provisional application No. 63/448,908, filed on Feb. 28, 2023.

(51) Int. Cl.
*G16H 40/63* (2018.01)

(52) U.S. Cl.
CPC .................................. *G16H 40/63* (2018.01)

(58) Field of Classification Search
CPC .............................. G16H 40/63; G16H 40/67
See application file for complete search history.

(56) References Cited

U.S. PATENT DOCUMENTS

2016/0088891 A1* 3/2016 Walsh .................... A42B 3/003
                                                          2/421
2020/0197107 A1* 6/2020 Ryan ...................... A61B 90/98

* cited by examiner

*Primary Examiner* — Seung C Sohn
(74) *Attorney, Agent, or Firm* — Garrett M. Smith

(57) ABSTRACT

A clinical personal protection equipment (PPE) system, worn by a healthcare provider, that can include a data display and selectively controls medical equipment. The system includes a computer platform that selectively communicates with a network, such as a Wifi network, and selectively communicates with and controls one or more electronic devices, such as an interactive rotating hemostatic valve and Tuohy-Borst adapter. The headset fits about the head of user and includes a face shield. A camera is located on the headset and is in communication with the computer platform, the camera creating visual data of a forward view from the headset and transmitting the visual data to the computer platform.

20 Claims, 8 Drawing Sheets

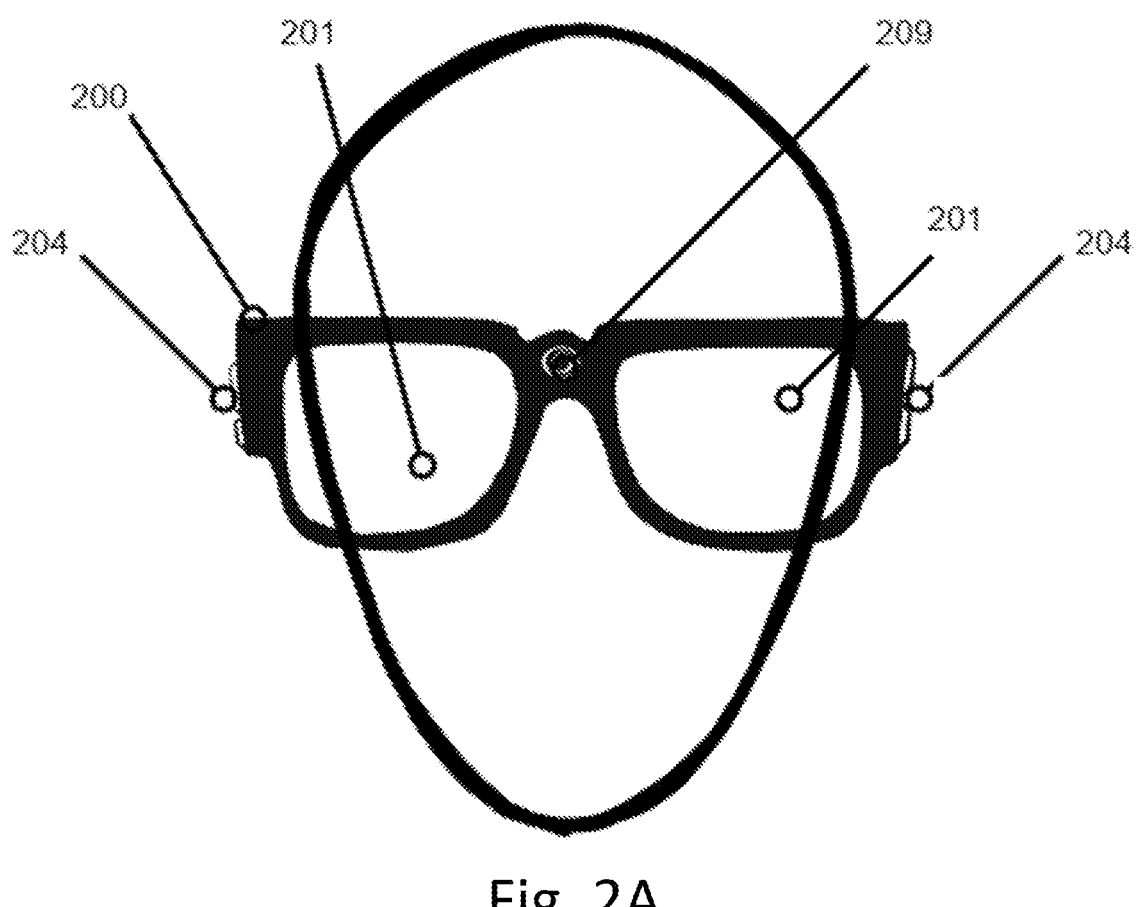
Fig. 2A
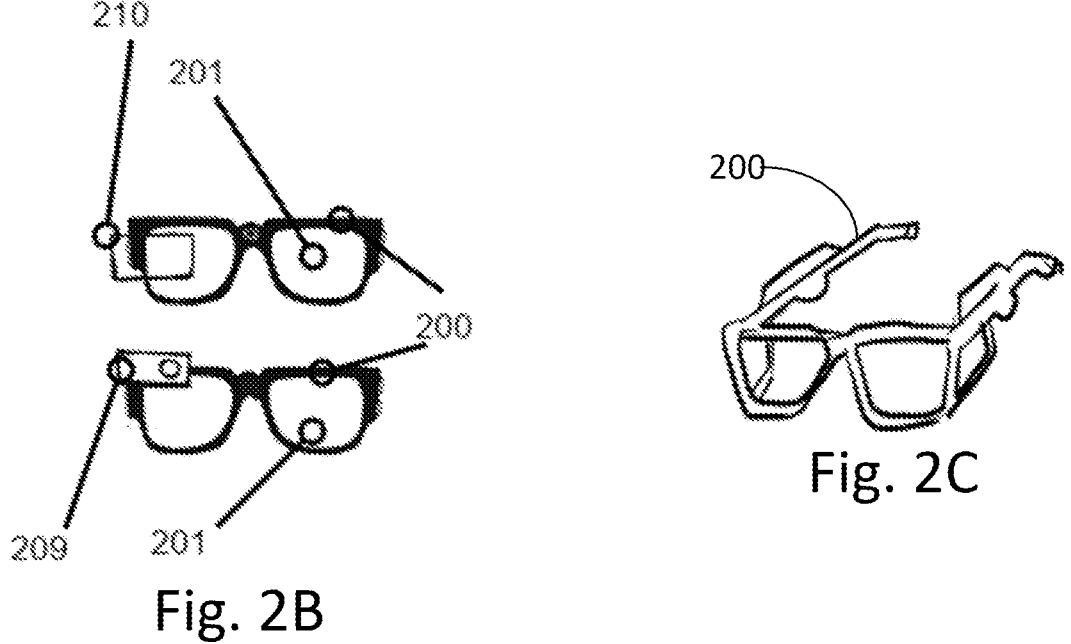
Fig. 2B
Fig. 2C

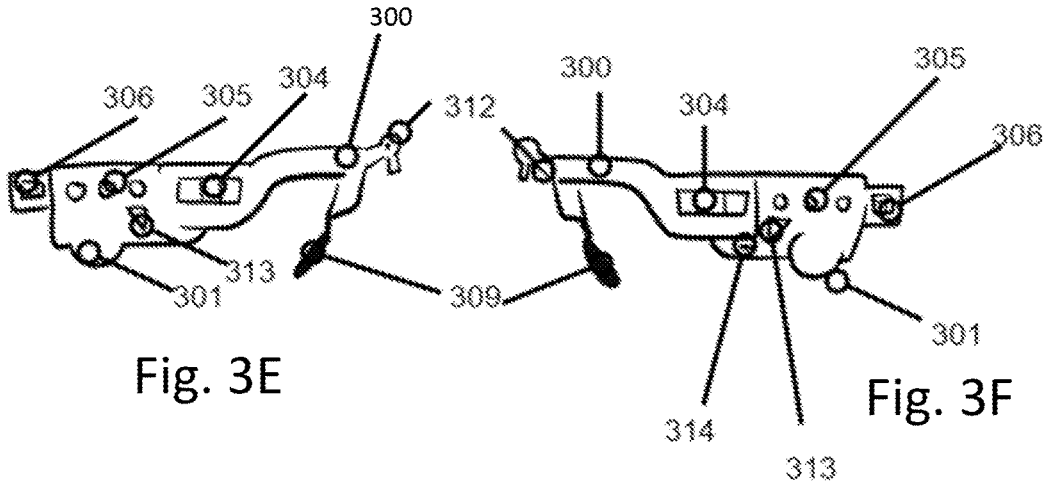
Fig. 3E
Fig. 3F
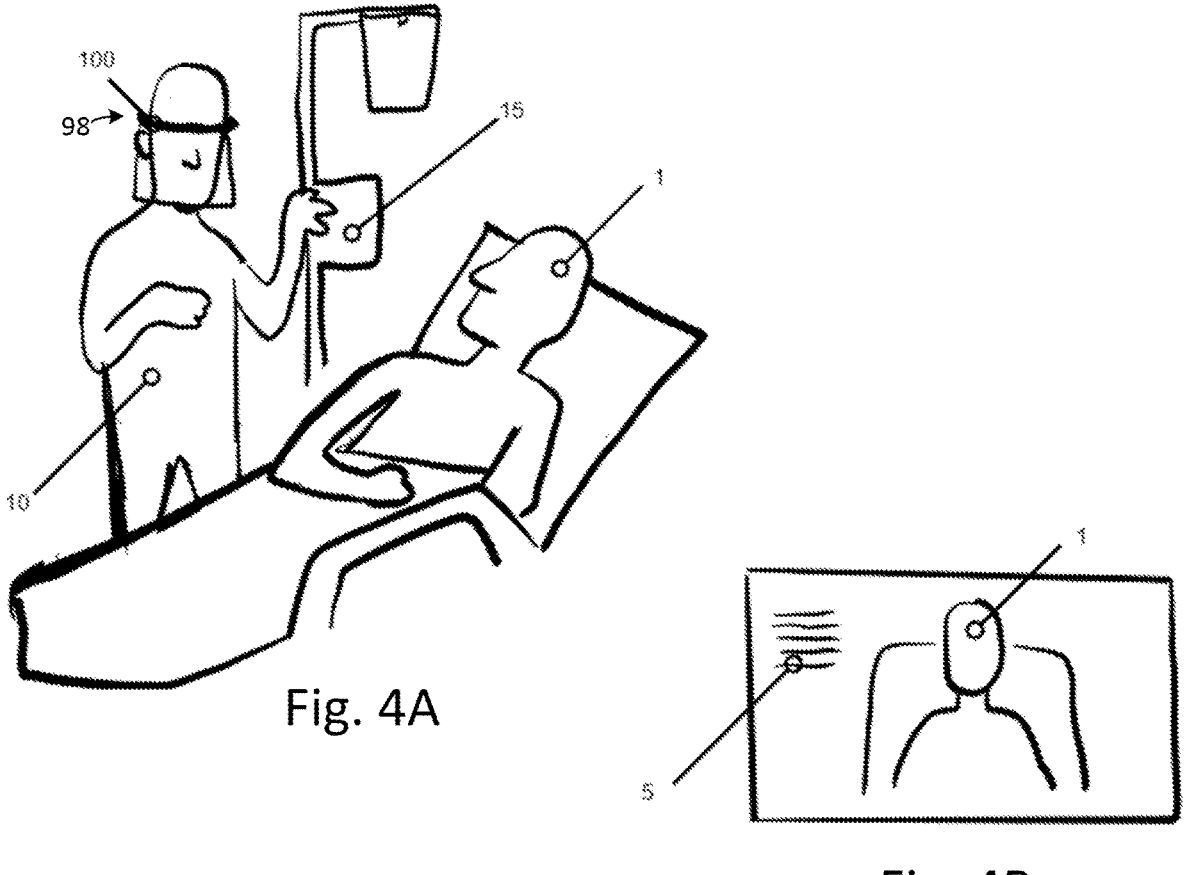
Fig. 4A
Fig. 4B

CLINICAL PERSONAL PROTECTIVE EQUIPMENT WITH INTEGRATED DISPLAY AND MEDICAL DEVICE CONTROL SYSTEM

BACKGROUND OF THE INVENTION

This application claims the benefit of U.S. Provisional Patent Application Ser. No. 63/448,908, filed Feb. 28, 2023, the entirety of which is incorporated herein by this reference.

BACKGROUND OF THE INVENTION

1. Field of the Invention

The present invention generally relates to medical devices and personal protective equipment (PPE). More particularly, the present invention relates to personal protective equipment including integrated displays and control systems for medical devices, and healthcare data capture, storage, and retrieval.

2. Description of the Related Art

In extant systems for healthcare data communication, especially at bedside, is very inefficient and non-discreet. The proliferating use of pagers and other telecommunication devices by healthcare professionals, in addition to personal cell phones with electronic health record applications, results in fragmentation of communication and distracts from efficient and personable delivery of health care. Responding to pages interrupts the work that the healthcare professional is currently involved in, and there is a growing list of devices employed in the daily work of front-line health care workers, a jumble of PPE and telecommunication devices. This does not include the user's personal devices necessary to stay in contact with family. The health care worker is cluttered, and communication is fragmented across devices, which can compromise workflow and efficiency.

There are currently few medical devices that consolidate communication functionality, electronic health record integration and PPE into a single aesthetically healthcare appropriate wearable technology. As can be seen, there is a need for improved PPE that facilitates communications with patients, other healthcare workers, portable communications and accessing data within the healthcare environment.

Moreover, interactive medical devices that allow the communication of healthcare data do not themselves typically allow the control of or interaction with medical devices that are in situ on the patient. For example, many medical devices lack integrated sensors for a capability to provide quantitative feedback to operators. Trainees and junior operators have to rely on high repetition of manual procedural technique with varying learning curves related to factors beyond control of the individual or hosting institution, e.g., varying case volumes due to proliferating competition in fields without coincident growth in case volume demand, geographic limitations and volatility related to unpredictable events such as the pandemic and its prolonged effect on elective procedures training to the detriment of trainee education as operators.

Beyond the initial acquisition of manual technical parameters for basic operative technique, there is variability in individual patient anatomy that imposes on a general "one-size-fits-all" approach to training. Given this known limitation, operators often spend valuable time trying to ascertain the optimal force necessary to exert on a catheter for any given task (e.g., thrombectomy, stent deployment, flow diversion, etc.). This additional time can tie down valuable operating room or angiography suite space for patient care. Additionally, excessive force or lack of appropriate force by the operator can lead to potentially devastating complications for patients (e.g. vessel avulsion/dissection, distal clot embolization, etc.) which can cause permanent neurologic deficit and death.

This problem is exacerbated with medical instrumentation lodged within the human body, such as catheters, wires, and probes. Currently, there are no adequate devices in this space that provide the ability to monitor wire/catheter force and rotational angulation in real-time, and interface these values onto an electronic display for operator use. The availability of such data would provide valuable diagnostic information that could be used to improve patient care and outcomes, and assist the provider in appropriate selection of catheters/wires/endovascular tools optimized for the individual procedure underway, informing safe practice and establishing an avenue for internal quality review (by linking with electronic health record and imaging data related to clinical and radiographic outcomes).

Accordingly, extant medical data communication devices and PPE equipment create a difficult environment for patient care. Furthermore, valuable medical data at bedside or medical procedure goes mostly uncaptured due to limited data recordation devices and storage capabilities. It is thus to address these problems with the prior art that the present invention is primarily directed.

BRIEF SUMMARY OF THE INVENTION

Briefly described, the present invention provides a clinical personal protection equipment (PPE) system, worn by a healthcare provider, that can include a data display and selectively control and interact with medical equipment. The system includes a computer platform that selectively communicates with a network and controls one or more electronic devices, such as medical device, and can gather medical data from a patient at a local bedside visit or procedure. The headset fits about the head of user and includes a face shield. A camera is located on the headset and is in communication with the computer platform such that the camera creates visual data of a forward view from the headset and transmits the visual data to the computer platform.

The PPE system includes a computer platform configured to selectively communicate with a network and further configured to selectively communicate and control one or more electronic devices. The system further includes a headset configured to selectively fit about the head of user, and has a face shield to protect the head and face of the user. The system includes a camera, located on the headset and in communication with the computer platform, that at least selectively creates visual data of a forward view from the headset and further selectively transmits the visual data to the computer platform.

The headset and face shield can be sterilizable, and the face shield can selectively detach from the headset. Further, one electronic device the computer platform can selectively communicate with can be a haptic interface. The computer platform and camera can be in wired or wireless communication with each other or across a network generally. The headset can further includes a display to the user, with the display communicatively connected to the computer platform. The computer platform can communicatively connect with medical equipment that is monitoring a patient, and selectively receive health data for the patient. The computer platform can also communicatively connect with a healthcare records database for health and selectively transmit and receive healthcare data to and from the health-care records database. For example, there can be analysis of data collected with correlations clinically and radiographi-cally verified that are used to demonstrate live data visual-izations with color coded spectrum and indicators of safety parameter on the display. This heads-up display can augment operator practice, individualize technique to patient's indi-vidual anatomy, and speed up trainees and junior operators' acquisition of fundamentals of technical safety. The data collected can also be used to inform safe parameters for automated steps or partial procedure automation as technol-ogy in robotics develops in the healthcare field.

One of the electronic devices the computer platform selectively communicates can be a novel rotating hemostatic valves (RHV) and Tuohy-Borst adapters (TBA) for use with catheter-based and other relevant procedures using a gener-alized co-axial compatible technical approach. The novel valve allows for measurement, recording, and display of force measurements exerted on catheters introduced through the novel device. The device is intended for use by health-care professionals for accurate measurement and reproduc-tion of force necessary to execute catheter-based tasks and can be integrated into simulation software programs for pre-procedural planning or operator and other related health-care trainee education.

The valve can be configured to accept catheters of various sizes and include rotating valves configured to be operator-adjusted to allow proximal support. The rotating valves can also include settings that are activated by haptic clicks, or other tactile, visual, or audible alerts.

The valve includes an integrated force transducer config-ured to measure various forces exerted on a catheter and output the measurement to the computer platform, and potentially a signal amplifier for the force transducers signal that receives the output, amplifies magnitude and reduces noise in the output, and relays the modified output to other computer devices. The computer platform can receive the modified outputs and display the force transducer signal to the user. In a further embodiment, the one or more electronic devices can be medical devices outputting medical data to the computer platform, and the computer platform stores received medical at one or more computer devices across the network, such as a cloud storage.

In one embodiment, the invention includes a method of recording and displaying medical data in a PPE system by capturing visual medical data a camera located on a PPE headset that is configured to selectively fit about the head of user, with the headset further including a face shield to protect the head of the user, and sending the visual medical data to a computer platform, with the computer platform configured to selectively communicate with a network and selectively communicate and control one or more electronic devices. The method continues with receiving the visual medical data at the computer platform, and displaying, through control with the computer platform, the medical data to the user. The display of the medical data to the user can be through display on the headset, through a separate screen or directly on the face shield.

The present invention therefore provides an advantage over the prior art in that the PPE equipment of the present invention allows real-time interaction with medical data and control of medical equipment during a medical procedure. The medical data can be stored in the patient's medical records for further use and diagnosis. The present invention has industrial applicability in that it is used to assist in the administration of heath treatment by medical providers, as well as provide for the storage and retrieval of valuable medical data for patients. These and other advantages of the present invention will become apparent to one of skill in the art after review of the present Drawings, Specification, and Claims.

BRIEF DESCRIPTION OF THE DRAWINGS

FIG. 2A is front view of an alternative design for one embodiment of headset with integrated voice and audio communications.

FIG. 2B is a front view of the headset design of FIG. 2A embodiment with an augmented reality screen and camera.

FIG. 2C is a perspective view of the headset of FIG. 2A.

FIG. 3E is a right-side view of one embodiment of the headset frame of FIG. 3A.

FIG. 3F is a left-side view of one embodiment of the headset frame of FIGS. 3A and 3E.

FIG. 4A is a perspective view of a user wearing a headset with a face shield during clinical practice at the bedside.

FIG. 4B is a perspective view of one embodiment of a visual data being captured by a camera on the headset in FIG. 4A, shown here as a data overlay on augmented reality screen to the user.

DETAILED DESCRIPTION OF THE INVENTION

Figures 1A, 1B, 1C, 1D:
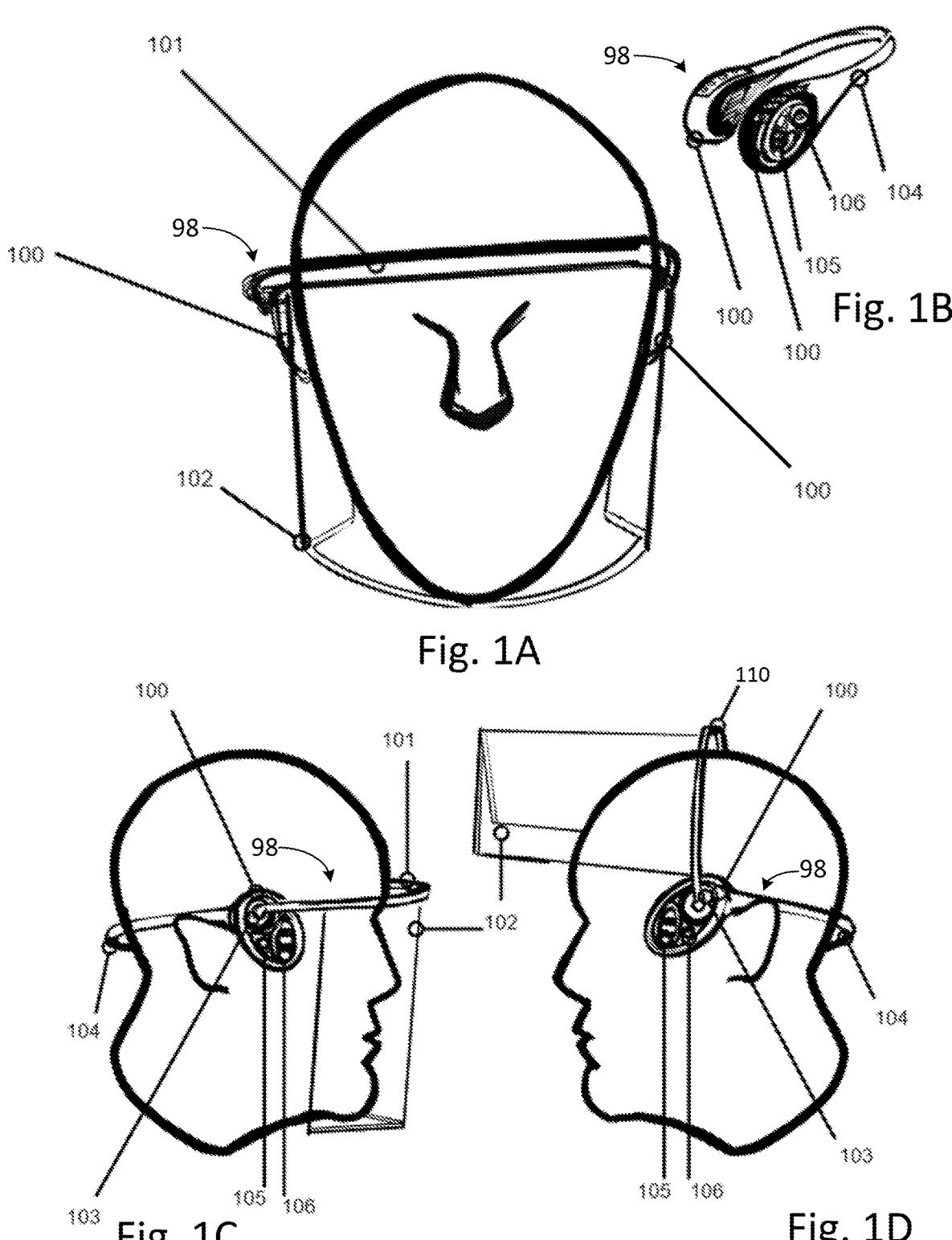
FIG. 1A is a front view of the headset with face shield embodiment of the clinical personal protective equipment with integrated voice and audio communications.
FIG. 1B is a perspective view of the headset with head-phones embodiment of the clinical personal protective equipment with integrated voice and audio communications.
FIG. 1C is a right-side view of the headset and head-phones of FIG. 1A-1B, with the face shield lowered.
FIG. 1D is a left-side view of headset and headphones of FIG. 1A-1C, with the face shield raised.

With reference to the figures in which like numerals represent like elements throughout the several views, FIG. 1A is a front view of the headset 98 with face shield 102 embodiment of the clinical personal protective equipment with integrated voice and audio communications. FIGS. 1A and 1B illustrate the headset 98, headband variant 104, face shield 102, shown here with integrated bone conduction headphones 100, and microphone with controls 105,106 and connection for charging embedded battery and attaching peripheral 10 attachments 107. FIG. 1B is a perspective view of the headset 98 with headphones 100. FIG. 1C is a right-side view of the headset 98 and headphones of FIG. 1A-1B, with the face shield lowered. FIG. 1D is a left-side view of headset 98 and headphones of FIG. 1A-1C, with the face shield 102 raised and the top 110 of the face shield 102 over the head of the user.

Figures 6A, 6B, 6C:
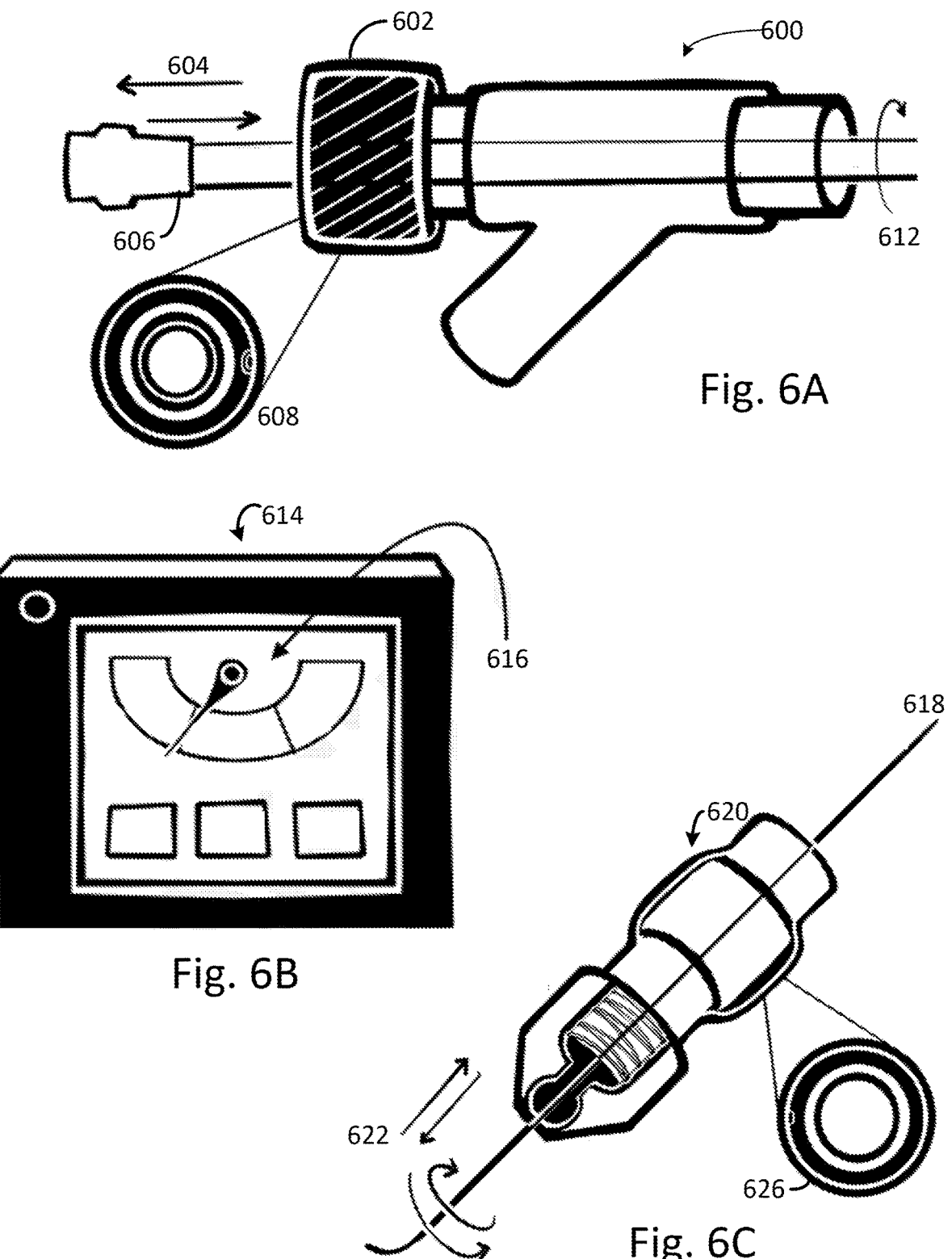
FIG. 6A is a side-view of one embodiment of a rotating hemostatic valve that is Tuohy-Borst adapter compatible with coaxial catheters and wires, which can be used with the headset and equipment of FIGS. 1A-5B.
FIG. 6B is a display of the data produced by the valve of FIG. 6A.
FIG. 6C is a perspective view of a catheter and wire used in the valve of FIG. 6A.

The headset 98 includes an embedded computer platform configured to selectively communicate with a network, such as the Internet, Wifi network, and the like, and further configured to selectively communicate and control one or more electronic devices, such as camera 209 in FIG. 2A or the valve 600 in FIG. 6A. The headset 98 is configured to selectively fit about the head of user, such as via headband 104 or adjustable band 307 in FIG. 3D, and in the embodiment of FIGS. 1A-1D, has a face shield 102 to protect the head and face of the user. The headset 98 preferably has a camera 209, as shown in FIG. 2A, located on the headset 200 and in communication with the computer platform, that at least selectively creates visual data of a forward view from the headset, as further shown in FIGS. 4A-4B and further selectively transmits the visual data to the computer platform.

The headset 98 and face shield 102 can be sterilizable, and the face shield 102 can selectively detach from the headset 98. The computer platform and camera can be in wired or wireless communication with each other, or communicate across a network generally.

Figures 2D, 2E:
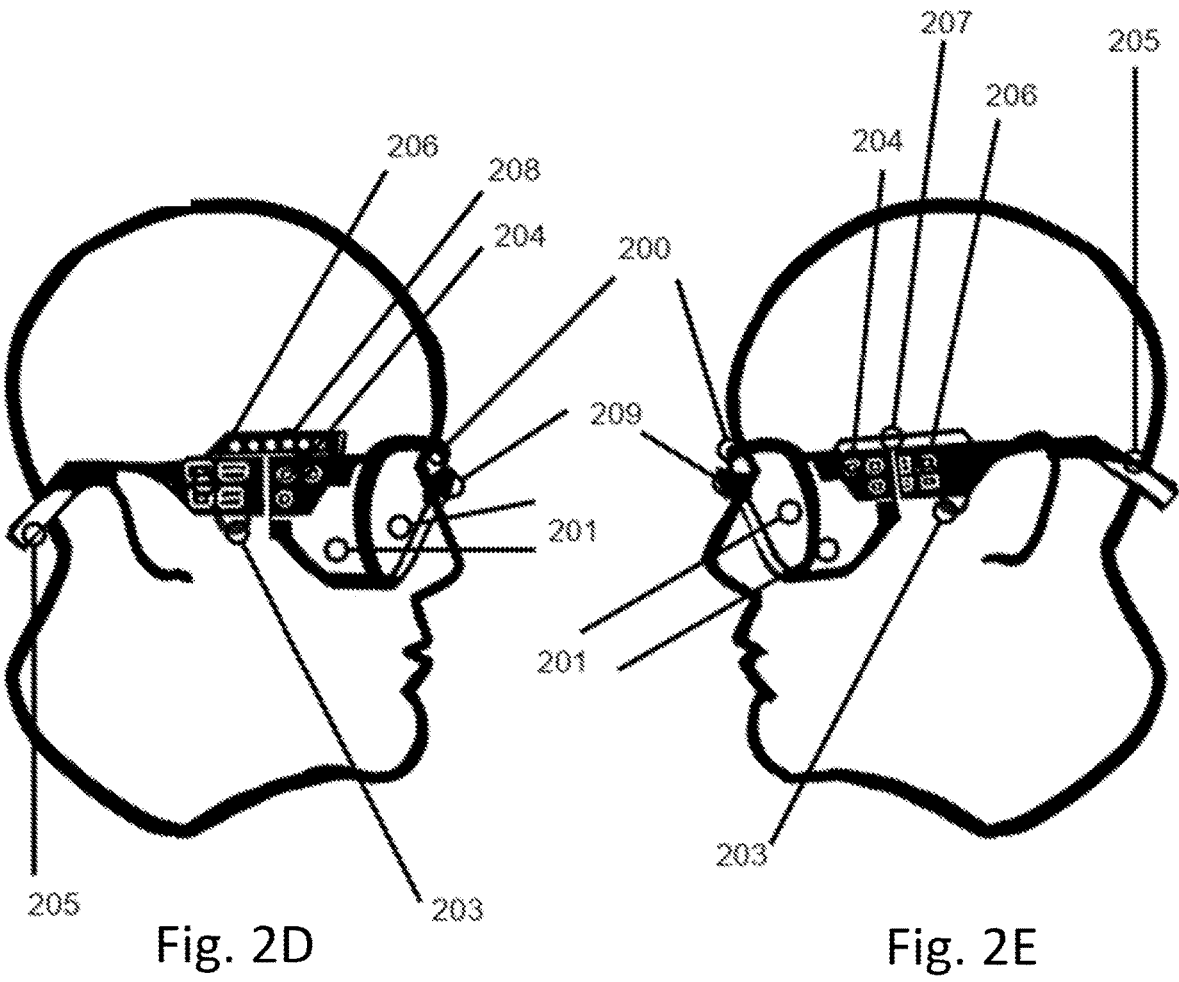
FIG. 2D is a left-side view of the headset embodiment of FIG. 2A.
FIG. 2E is a left-side view of the headset embodiment of FIG. 2A.

FIGS. 2A-2E illustrate one embodiment of the headset embodied as googles 200 with peripheral attachments camera 109 and augmented reality screen 210. FIG. 2A is front-view of an alternative design for one embodiment of headset as googles 200 with integrated voice and audio communications. FIG. 2B is a front view of the googles 200 design of FIG. 2A embodiment, and FIG. 2C is a perspective view of the headset of FIG. 2A. FIG. 2D is a left-side view of the headset embodiment of FIG. 2A. FIG. 2E is a left-side view of the headset embodiment of FIG. 2A.

The goggles 200 offer radiation protection with leaded lenses 201 and have frames with an optional embedded camera 209. Exemplary placement of device controls and indicator lights are shown on control pad 204, with additional controls for programmable functions 206 and open-air bone conduction headphones 203, with behind the ear frame arms or adjustable band 205. Exemplary locations for attachment for peripherals 208 and side frame embedded battery 207 are shown. FIG. 2A shows the device worn in frontal view, FIG. 2B shows the device in isolation with camera 209 and augmented reality screen 210 attachments shown in frontal view.

Figure 3A:
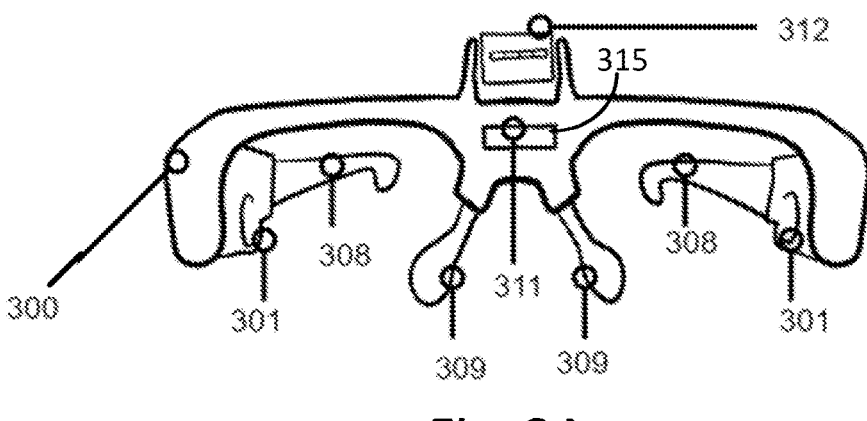
FIG. 3A is a front-view of one embodiment of the headset frame without a face shield attached.
Figure 3B:
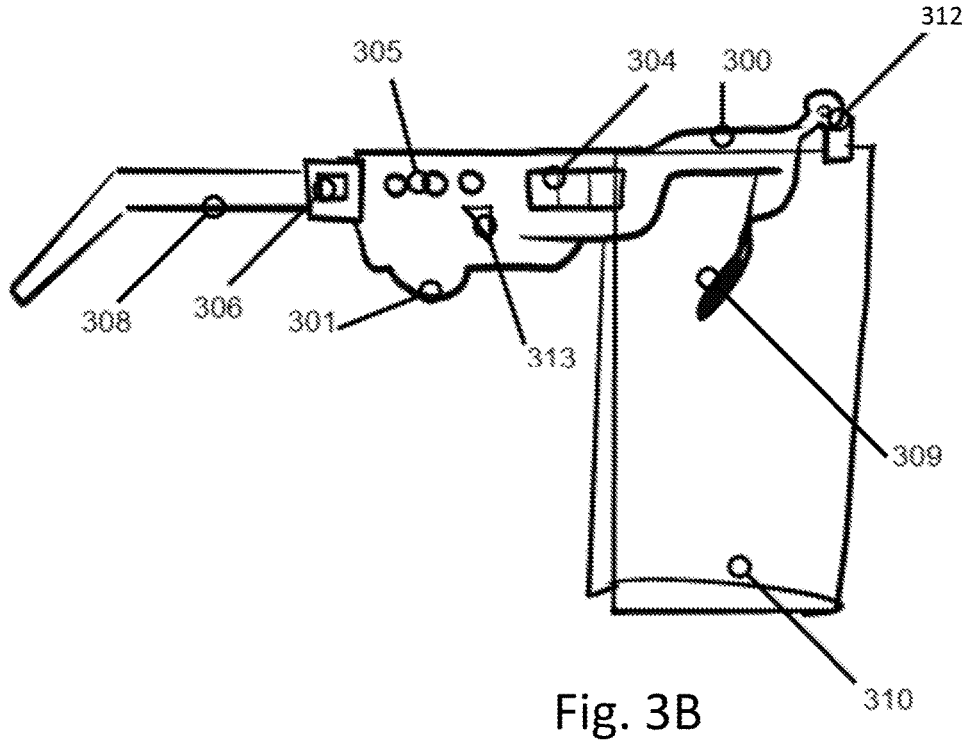
FIG. 3B is a left-side view of the headset of FIG. 3A with the face shield attached thereto.
Figure 3C:
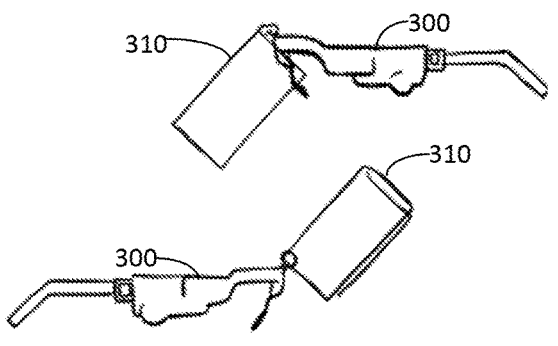
FIG. 3C is a left and right-side view of the headset of FIGS. 3A-3B with face shield partially and fully lifted.
Figure 3D:
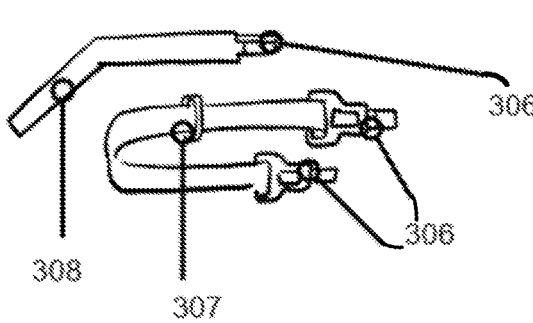
FIG. 3D is a side perspective view of an embodiment of a rigid headset frame and adjustable band to hold the headset to the user.

FIG. 3A is a front-view of one embodiment of the headset as a frame 300 with a nose bridge 309 and a face shield 310 not yet attached. FIG. 3B is a left-side view of the headset of FIG. 3A with the face shield 310 attached thereto. FIG. 3C is a left and right-side view of the headset of FIGS. 3A-3B with face shield partially and fully lifted. FIG. 3D is a side perspective view of an embodiment of a rigid headset frame 300 and adjustable band 307 to hold the headset to the user. FIG. 3E is a right-side view of one embodiment of the headset frame 300 of FIG. 3A, and FIG. 3F is a left-side view thereof.

As shown in the embodiment of FIGS. 3A-3E, the frame 300 has an attachment 312 for a face shields 310, which can be a full or half visor. Wearable frame 300 fits the head of a user with either a rigid glasses frame arm 308, or as shown in FIG. 3D as adjustable band 307 using compatible interchangeable snap fit attachment 306 to frame body 300. FIG. 3B illustrates exemplary controls 304 and indicator lights placement 305, along with location of bone conduction headphones 301 and microphone 314. In this embodiment, there is a forward location in frame bridge 311 for light and embedded camera 315. There is an additional control button 313 and an attachments site 312.

With the present headset 300, a healthcare professional (or worker) can customize use of personal protective equipment and communications device based on function that is task appropriate. The user interchanges peripherals (which attach to side of frame 300, can detach face shield 310 (customize shield use; full face or visor/goggle 200) when desired, with easy cleaning of the device with sterilizing wipe (standard availability in healthcare settings for cleaning PPE in between patient encounters), device parts can be recycled and replaced (e.g., face shield if damaged or change of coverage is desired (full face versus visor), updates to form and peripherals.

The present system using the headset 100 combines hands free, and discrete method to communicate with other healthcare professionals without disrupting workflow. The headset can be embodied as a flexible frame 300 that can attach protective gear (masks and face shield) and is customizable with easy-to-connect peripherals utilizing a modular design. The embedded microphone 105 allows for two-way communication with an electronic health record to document at the bedside for real-time clinical dictation (as more fully shown in FIGS. 4A-4B), and the bone conduction headphones 203 provides a more discrete, private messaging that will not be heard by others nearby, maintaining patient privacy with communicating potentially sensitive clinical information between providers. The use of bone conduction headphones 203 for audio alerts for user comfort and all-day open ear wear.

The peripherals for the headset 300 are expandable to include a camera 315 that enables the user to record clinical encounters for safety, educational or training purposes, the face shield 310 can be removable and recyclable. Attachments to the frame 300 include variations to incorporate an augmented reality screen 210 to the frame 200, in anticipation of the growing use of augmented reality in the delivery of healthcare, and potential for more sophisticated representation of data retrieved from the electronic health record, including clinical documentation of encounters, laboratory results and imaging. Allowing user more seamless integration with the electronic health records to increase time spent at the bedside fostering a better patient-provider relationship, as the work of documentation and data retrieval is brought seamlessly to the bedside without fragmenting the encounter with interruptions and straining the patient-provider relationship.

The computer platform can interface with current electronic devices utilizing electronic health record systems software applications which allow for retrieval of lab values and imaging through the user's personal device display 210. The device screen 210 can be used to display numeric and character data such as lab values and clinical notes, screen peripheral allows for augmented reality and ability to review prior imaging. Connection can occur over Bluetooth® with other electronic devices, or another wireless standard, such that integration with applications using electronic health records to receive alerts, communication. This also allows for health worker documentation using verbal dictation.

As shown in FIGS. 2A-2E, the headset may also be embodied in goggles 200 for radiation protection with lead lenses, for use by healthcare providers using fluoroscopy and doctor practicing interventional radiology (includes all specialties involved in fluoroscopy guided procedures, e.g., neuro intervention, vascular surgery and interventional (body) radiology). The embedded open ear headphone system (bone conduction 203, with future iterations using small speaker) allow for seamless communication while maintaining awareness of the environment and team members in the physical space. The peripheral attachment augmented reality screen 210 (or view finder camera screen) allows for intra operative data retrieval, including review of previous imaging and relevant complex neuroanatomy (connectivity with control room, allows technologist to select desired information/references and send to the doctor scrubbed in the sterile field). Doctors performing interventional radiology and neuro radiology procedures are now able to stay connected without having to interrupt the procedural workflow. Silent option can also be engaged when doctor desires to further minimize distractions during critical stages of a procedure. The augmented reality screen 210 is also used to send critical lab values or vital signs to the operator, further enhancing team communication and unified action.

As shown in the several embodiments of the headset 98, 200, 300, the ergonomic design of headset frame can be embodied in multiple forms: Head band frame 98, flip-up frame 300, nose bridge frame, behind the ear frame 200, or strap-adjusted 307. Furthermore, the controls can be embedded in frame (on either side as shown in goggles 200 or frame 300, with haptic response to control power, volume, and combination for managing calls. There can also be an On/Off button, customizable selection button for peripherals control (controlled through software application accessed by the user on their personal electronic device), rocker button for controlling volume. The headset 300 can also vibrate for silent alert.

As further described herein, a camera 209 is attached to or integrated in the headset 200 for enhanced documentation of clinical encounters and education for remote learners, use in tele proctoring of junior clinical trainees using Wi-Fi connectivity transmitted over hospital internet network to remote learners at a different campus or expert providing remote expertise through proctoring of procedure. Attached to the side of the device frame 300 (affixed using strap or magnetic connectors), can also be the power derived for the frame and/or combination with external battery source, such as a rechargeable embedded battery, or the headset 98 can be charged with cable or device case with dock.

The headset, such as goggles 200, can also include a mini-viewfinder sized screen with remote connectivity to allow for reference of previous radiology scans, intra operative fluoroscopic pictures (accessed from control room), and anatomical reference, short videos of procedural technique or device prep (including device recommended instructions for use) can also be accessed, further advancing the proceduralist's skill set and procedural safety. When so embodied, an augmented reality protective shield allows for super imposed data on user's field of view, affording user enhanced sophistication with depth of data retrieval at the bedside, to assist with diagnosis, delivery of therapeutics and safety of care (facilitated by real-time data retrieval, negating risk of missed data and or interrupting care for retrieval of more sophisticated clinical content), such as with augmented reality screen 210.

In some embodiments, the system can be used with electro encephalography (EEG) forehead and scalp sensors for detection of user raw EEG data that used to program functions for control of external devices (e.g., biplane fluoroscopy table), program stores data and can retrieve angles that provided pathology specific optimal views. The data can be retrieved through Bluetooth® connected application on users preferred electronic device. This improves user's intra procedural workflow and efficiency as the user engages the computer brain interface program to control the fluoroscopy machine's camera angles without the need to interrupt manual performance of a procedure (such as catheterizing a vessel or cannulating a vein percutaneously), allowing for more focus on the critical tasks of the invasive procedure. Controls for basic functionality can be programmed for magnification and resolution, accessing standard view projections, and control of bi-plane software (e.g road map guidance, storing images or sequences). The user is also able to control views more remotely with use of the computer brain interface read of EEG data from the headband, the user is saved from radiation exposure by operating from the control room or further away from the radiation source, thus further limiting operator radiation exposure.

FIG. 4A is a perspective view of a user 10 wearing a headset 98 with a face shield during clinical practice at the bedside with a patient 1. FIG. 4B is a perspective view of one embodiment of a visual data being captured by a camera on the headset 98 in FIG. 4A, shown here as a data overlay on augmented reality screen to the user. FIG. 4A illustrates an example of the user 10 wearing face shield personal protective and headset 98 with a communication device 100 in use at the bedside. This is an example of dosing adjustment of intravenous medication 15 being delivered to the patient 1 based on real time electronic health record data retrieval (e.g. laboratory values) using the device shown in FIG. 4B. FIG. 4B shows the user's 10 point of view with augmented reality screen 5 peripheral showing the overlay of patient data.

Figures 5A, 5B:
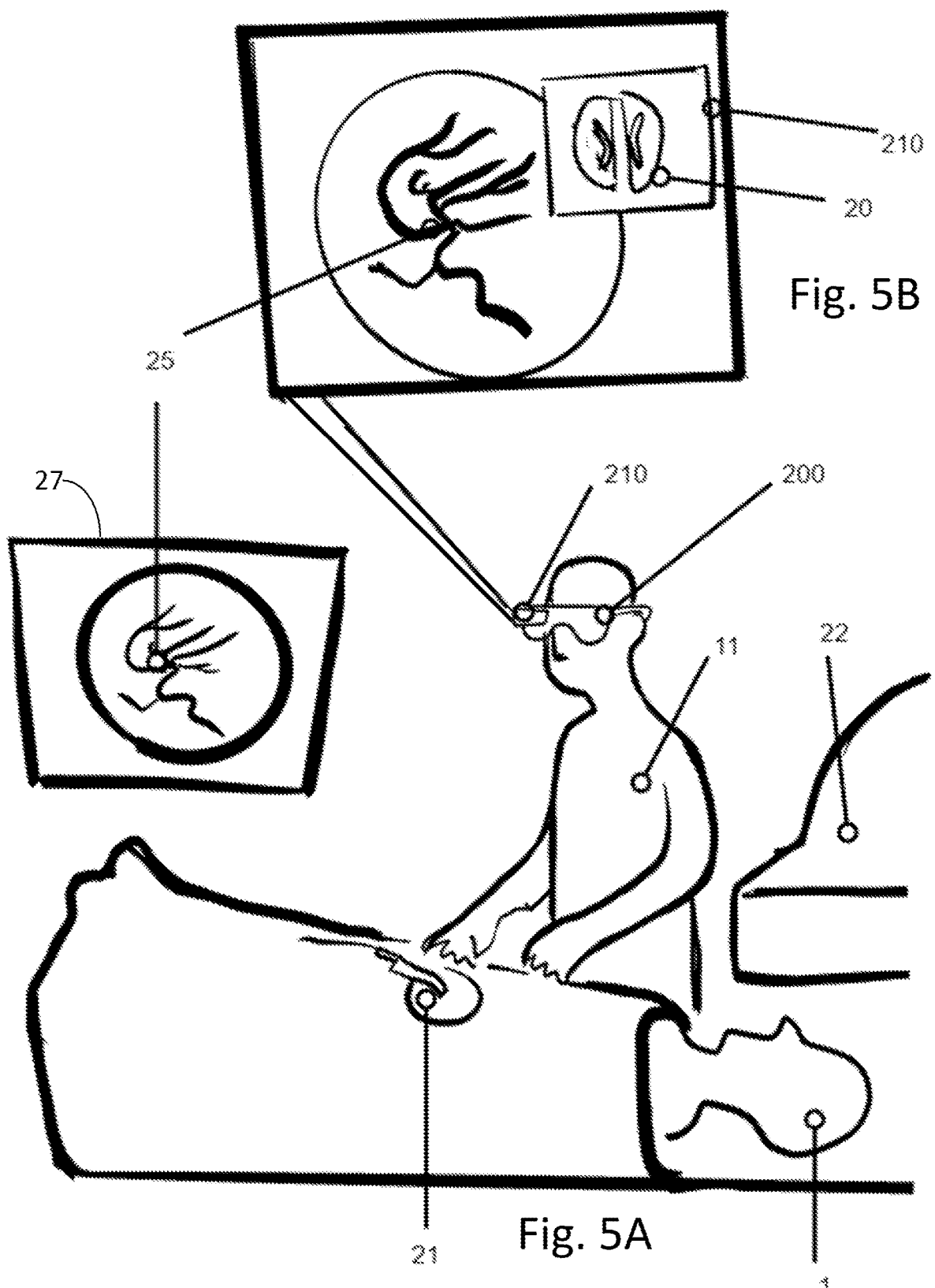
FIG. 5A is a perspective view illustrating a user wearing a headset embodied as radiation protection goggles device during clinical practice using x-ray technology.
FIG. 5B is a magnified inset showing the perspective and example of imaging overlay on the user's augmented reality screen on the headset.

FIG. 5A is a perspective view illustrating a user 11 wearing a headset 200 embodied as radiation protection goggles device (FIGS. 2A-2E) during clinical practice using x-ray technology. FIG. 5B is a magnified inset showing the perspective and example of imaging overlay on the user's augmented reality screen 210 on the headset goggles 200. In this example of radiation protection, goggles 200 are used intraoperatively during procedure requiring fluoroscopy 22 with augmented reality display 210 in use. FIG. 5B shows user's 11 point of view with overlay of previous imaging 20 on live angiography 25, and the exam of transfemoral 10 percutaneous 21 catheter angiography performed on a supine patient 1 is shown.

FIG. 6A is a side-view of one embodiment of a rotating hemostatic valve 600 that is Tuohy-Borst adapter compatible with coaxial catheters 606 and wires 618, which can be used with the headset 98 and equipment of FIGS. 1A-5B. Tuohy-Borst adapters are well known in the art and are designed to facilitate catheter introduction and are intended for interventional and diagnostic procedures.

FIG. 6B is a display 614 of the validated parameters 616 produced by the valve of FIG. 6A. FIG. 6C is a perspective view of a catheter 606 and wire 618 used in the valve of FIG. 6A. The embodiment and parts of the rotating hemostatic valve 600 capture forces transmitted by the operator performing percutaneous fluoroscopic guided endovascular procedures.

The valve 600 contains sensors which capture these forces including (but not limited to) load 612, and rotation of the catheter 606 and wire 618. Other force measurements such as velocity, torque, or torsion can also be measured. This data is then projected on heads up display 614 for augmented visual feedback of operative technique 616 and live correction to maintain data value within validated parameters 616. The embodiment and parts of the torque device 620 with embedded sensors 626 in the proximal segment 626 of the device 620 and the screw-on segment which grips compatible co-axial wires 618 for control of torque 622. Sensors transmit data wirelessly to the heads-up display box 614 displaying data collected 616 with validated data being displayed with color coded segments (or other visual classification) to maintain operator forces within validated parameters 616 for a given procedure. The rotating valve knob 602 is shown with a cross-section 608 of the knob 602. The rotation of the knob 602 will advance and retract a catheter 606 and/or wire 618.

Figures 7A, 7B:
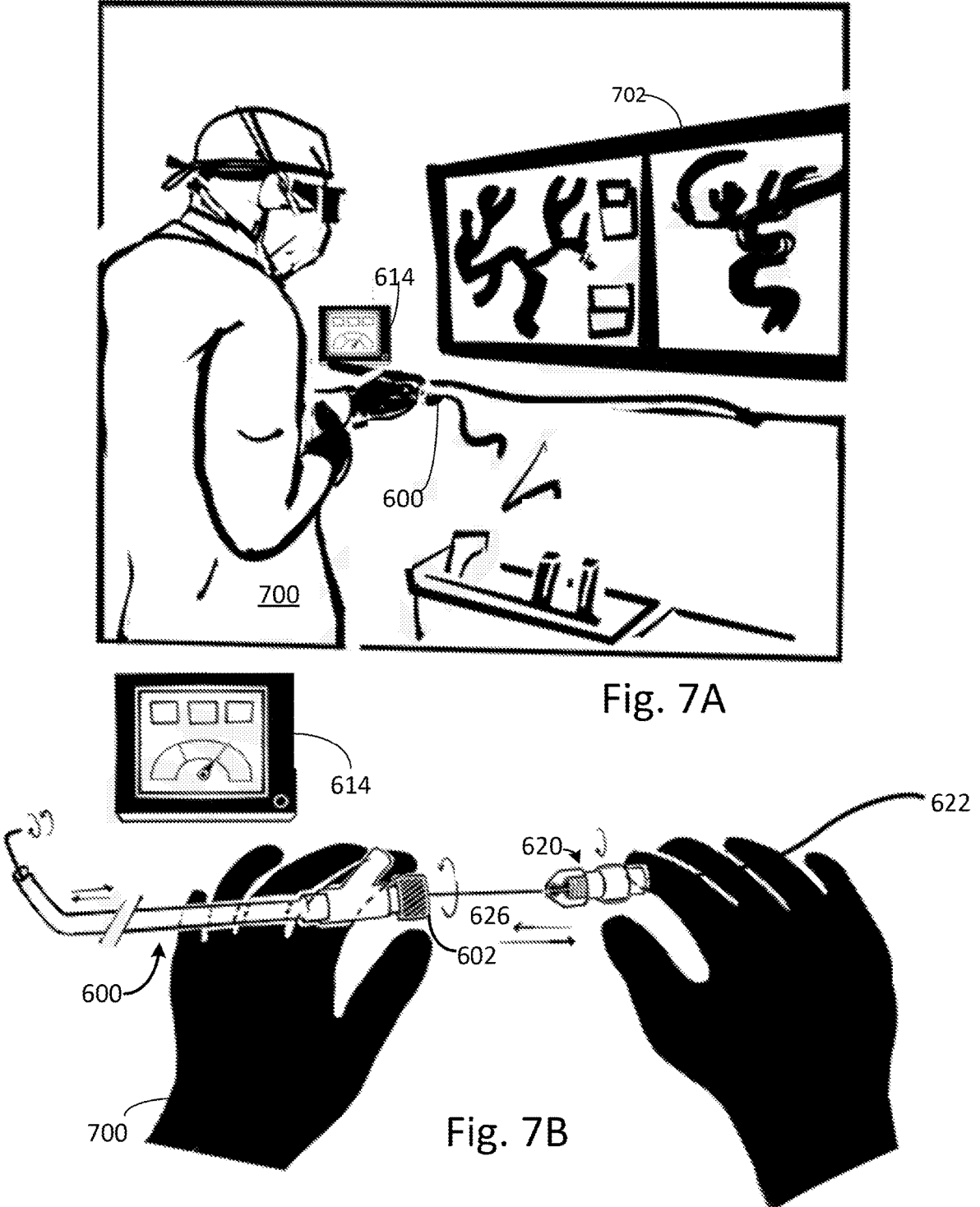
FIG. 7A is a perspective view of a user of the valve and instruments of FIGS. 6A-6C to perform an endovascular procedure.
FIG. 7B is a perspective view of the use of the valve, catheter, and wire of FIGS. 6A and 6C.

FIG. 7A is a perspective view of a user 700 of the valve 600 and instruments of FIGS. 6A-6C to perform an endovascular procedure. FIG. 7B is a perspective view of the use of the rotating valve 600, catheter 606, and wire 622 of FIGS. 6A and 6C. The operator 700 transmits forces on a co-axial system 626, captured by sensors in the valve 600, and torque are displayed on a heads up display 614 to augment feedback of the operative technique during percutaneous endovascular procedures. The valve 600 is devised to be universally compatible with catheters 606 and wires 622 of varying sizes that are employed in practice. The data collected can be used to correlate with clinical outcomes for employment in continuous quality improvement initiatives.

Embodiments of the valve 600 include force transducers (or load cells) that convert mechanical force (including such measures such as load, weight, tension, compression, and pressure) exerted by introduced catheters into an electrical signal output that changes proportionally to the amount of force exerted. Multiple transducers can be used to measure forces acting in different planes of motion and these transducers can be connected in a circuit. The electrical output signal from these transducers can be conditioned with an amplifier to increase signal to noise parameters before being processed by microprocessors, proximity sensors, or data acquisition modules. Ultimately, this processed data will then be displayed to the operator/user on an electronic screen for easy viewing, such as on display 614.

Once the measurements have been obtained, the data can be stored locally and/or in a cloud storage space. These measurements can then be retrieved again for use during another similar procedure, or in a simulation environment for training purposes. The database can store clinical outcomes (e.g., modified Rankin Scale, NIH Stroke Scale, mortality, hemorrhage, stroke, myocardial infarction, dissection, etc.) and radiographic outcomes (e.g., extent of reperfusion, fluoroscopy time, time to first pass recanalization, etc.). Over time, as the collected dataset grows, prediction models for optimal catheter forces can be derived. The invention apparatus would then be able to calculate a predicted optimal force and display this as a reference for operator use interprocedurally, while simultaneously measuring exerted force in real-time for comparison.

The reference point can also be bounded on the upper end to represent force thresholds for increased risk of vessel avulsion or dissection after analysis of collected data over time. A lower bound can also be obtained for certain tasks (e.g., mechanical thrombectomy) where inadequate force can also lead to complications (e.g., distal embolization. An operator can use this device during performance of a catheter-based procedure in place of conventional RHVs and TBAs for various catheter-based procedures/tasks (e.g., mechanical thrombectomy, aneurysm coiling, coil embolization, vessel angioplasty and/or stenting, vessel flow diversion, intravascular thrombolysis, transaortic valve implant/replacement, left atrial appendage/foramen ovale closure). Once the device is in place, the operator will introduce a catheter and/or wire through the device, the presence of which will be detected by various force transducers/load cells incorporated into the device. During the procedure, the operator will be able to see real-time measurements of forces exerted on the system and the corresponding reference for optimal force and threshold forces for increased complication rates. Once the procedure is finished, the measurements are stored for future retrieval and/or data analysis.

Alternatively, an operator or healthcare trainee can use this device in a healthcare simulation setting, either for pre-operative planning or for educational training. The device can be used in place of conventional rotating valves and Tuohy-Borst adapters that are currently used in various endovascular simulators. A previously performed case can be loaded for training purposes, or a new case can be prepared as per the individual simulator's settings (extraction of CTA, MRA, or DSA data). The case can then be run with the current device data 616 providing reference data for optimal force and threshold for increased complication rate. By practicing with this data, trainees can develop fine motor control and coordination to degrees that are used in real-world settings.

In one embodiment, the rotating hemostatic valve 600 and Tuohy-Borst adapter with modified valves (generalized to fit standard coaxial systems) can accept catheters of various sizes readily available on the market today. The valve 600 features rotating valves that are operator-adjusted, such as through knob 602, to allow for immobilization of the catheter 606 or simply to provide additional proximal support. The valves will have additional settings that are activated by haptic "clicks," which can allow the operator to begin or turn off force or other measurement recordings and/or display, which occur at certain rotational points of the knob 602.

The valve 600 can also be embodied with force transducers/load cells that can measure various forces exerted on catheter 606 in different planes and convert the signal into an electrical output that is relayed to a signal amplifier. There can be an amplifier, which could be in display 614, that is external to the force transducers/load cells, the amplifier receives input from them and conditions the signal by amplifying magnitude and reducing noise, then relays to microprocessors, proximity sensors, and/or data acquisition modules.

The display 614 can be embodied as receiving processed electrical signal outputs and displays values to show real-time forces, such as parameters 616, exerted on catheter 606. The display 614 can also be connected to a cloud database and able to show predicted optimal force, and threshold forces associated with increased complications rates. The cloud storage can include a data analysis network that, in one embodiment, stores HIPAA-compliant data (non-patient identifiable) regarding forces used during the procedure. Clinical outcome data and radiographic outcomes data are obtained from separate datasets submitted by operators for additional analysis over time to derive optimal force references as well as thresholds for increased complication rates.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A personal protection equipment (PPE) system, comprising:

a computer platform configured to selectively communicate with a network, the computer platform further configured to selectively communicate and control one or more electronic devices;

a headset configured to selectively fit about a head of a user, the headset further including a face shield to protect the head of the user; and a camera located on the headset and in communication with the computer platform, the camera at least selectively creating visual data of a forward view from the headset, wherein the camera further selectively transmits the visual data to the computer platform.

2. The system of claim 1, wherein the headset and face shield are sterilizable.

3. The system of claim 1, wherein the face shield is configured to selectively detach from the headset.

4. The system of claim 1, wherein at least one of the electronic devices the computer platform selectively communicates with is a haptic interface.

5. The system of claim 1, wherein the computer platform and camera are in wired communication, and the computer platform is in wired communication with the network.

6. The system of claim 1, wherein the computer platform and camera are in wireless communication, and the computer platform is in wireless communication with the network.

7. The system of claim 1, wherein the headset further includes a display to the user, and the display is communicatively connected to the computer platform.

8. The system of claim 1, wherein the computer platform is further configured to communicatively connect with medical equipment that is monitoring a patient, and the computer platform selectively receives health data for the patient.

9. The system of claim 1, wherein the computer platform is further configured to communicatively connect with a healthcare records database for health and selectively transmit and receive healthcare data to and from the healthcare records database.

10. The system of claim 1, wherein at least one of the electronic devices the computer platform selectively communicates with is a rotating hemostatic valve and Tuohy-Borst adapter, the valve configured to selectively connect to a catheter.

11. The system of claim 10, wherein the valve is configured to accept catheters of various sizes.

12. The system of claim 10, where the valve includes rotating valves configured to be operator-adjusted to allow proximal support.

13. The system of claim 12, wherein rotating valves include settings that are activated by haptic clicks.

14. The system of claim 10, wherein the valve includes an integrated force transducer configured to measure various forces exerted on a catheter and output the measurement to the computer platform, the force transducer having a signal thereof.

15. The system of claim 14, further including a signal amplifier for the force transducers signal, the amplifier configured to receive the output, amplify magnitude and reduce noise in the output, and relays a modified output to other computer devices.

16. The system of claim 15, wherein the computer platform is further configured to receive the modified outputs and display the force transducer signal to the user.

17. The system of claim 1, wherein the one or more electronic devices are medical devices outputting medical data to the computer platform, and the computer platform is further configured to store received medical at one or more computer devices across the network.

18. A method of recording and displaying medical data in a personal protection equipment (PPE) system, comprising:

capturing visual medical data by a camera located on a PPE headset that is configured to selectively fit about a head of user, the headset further including a face shield to protect the head of the user;

sending the visual medical data to a computer platform, the computer platform configured to selectively communicate with a network and selectively communicate and control one or more electronic devices;

receiving the visual medical data at the computer platform; and displaying, through control with the computer platform, the medical data to the user.

19. The method of claim 18, wherein the display of the medical data to the user is through display on the headset.

20. A personal protection equipment (PPE) system for capturing medical data, comprising:

a control means for selectively controlling one or more electronic devices, the control means further selectively communicating with a network;

a headset means for selectively fitting about a head of user, the headset means further including a face shield to protect the head of the user; and a camera means for selectively capturing visual data of a forward view from the headset means, the camera means located on the headset means and in communication with the control means, the camera means further selectively transmitting visual data to the control means.

\* \* \* \* \*